United States Patent [19]

Yanda

[11] 4,413,633
[45] Nov. 8, 1983

[54] METHOD AND APPARATUS FOR MONITORING BODY CONDITIONS

[76] Inventor: Roman L. Yanda, 462 Daniels Dr., Beverly Hills, Calif. 90212

[21] Appl. No.: 269,259

[22] Filed: Jun. 1, 1981

[51] Int. Cl.³ .............................................. A61B 5/00
[52] U.S. Cl. .................................. 128/736; 128/771; 128/204.22; 604/318; 604/901; 374/148
[58] Field of Search ............. 128/736, 350 R, 350 V, 128/295, 761, 768, 771, 204.22; 604/901, 318; 374/148

[56] References Cited

U.S. PATENT DOCUMENTS

| 605,178 | 6/1898 | Ferguson | 604/901 |
|---|---|---|---|
| 1,390,500 | 9/1921 | Christian | 604/901 |
| 3,460,395 | 8/1969 | Shaw | 128/295 X |
| 3,526,134 | 9/1970 | Paine | 374/148 |
| 3,543,743 | 12/1970 | Foderick | 128/295 X |
| 3,754,220 | 8/1973 | Sztamler et al. | 128/771 X |
| 3,769,497 | 10/1973 | Frank | 128/295 X |
| 3,818,895 | 6/1974 | Stewart | 128/736 |
| 3,871,229 | 3/1975 | Fletcher | 128/214 C X |
| 4,024,873 | 5/1977 | Antoshkiw et al. | 604/96 |
| 4,286,590 | 9/1981 | Murase | 128/771 X |

FOREIGN PATENT DOCUMENTS

| 72576 | 10/1916 | Austria | 128/736 |
|---|---|---|---|
| 264607 | 6/1970 | U.S.S.R. | 128/736 |

OTHER PUBLICATIONS

Ellenwood et al., IBM Tech. Discl. Bull., vol. 11, No. 11, Apr. 1969, p. 1565.

Primary Examiner—Kyle L. Howell
Assistant Examiner—John C. Hanley
Attorney, Agent, or Firm—Christie, Parker & Hale

[57] ABSTRACT

Body monitoring apparatus for use with a catheter tube having an outlet opening and a drainage tube having a male connector engageable with the outlet opening of the catheter tube. The apparatus comprises a tubular body member having at one end a male connector engageable with the outlet opening of the catheter tube, at the other end an outlet opening engageable with the male connector of the drainage tube, and an exit from the body member between the connector and the outlet opening. A flexible transmission line extends from a condition sensing transducer such as a temperature sensor through the body member from the male connector thereof through the exit to a point outside the body member. The exit is sealed to prevent leakage of fluid at the point of egress of the transmission line. In another embodiment, the intermediate tube has a window to permit outside observation of the interior of the tube. One or more temperature responsive visual indicators are located in the intermediate tube at the window. The indicators respond to different temperatures.

8 Claims, 3 Drawing Figures

U.S. Patent  Nov. 8, 1983  4,413,633
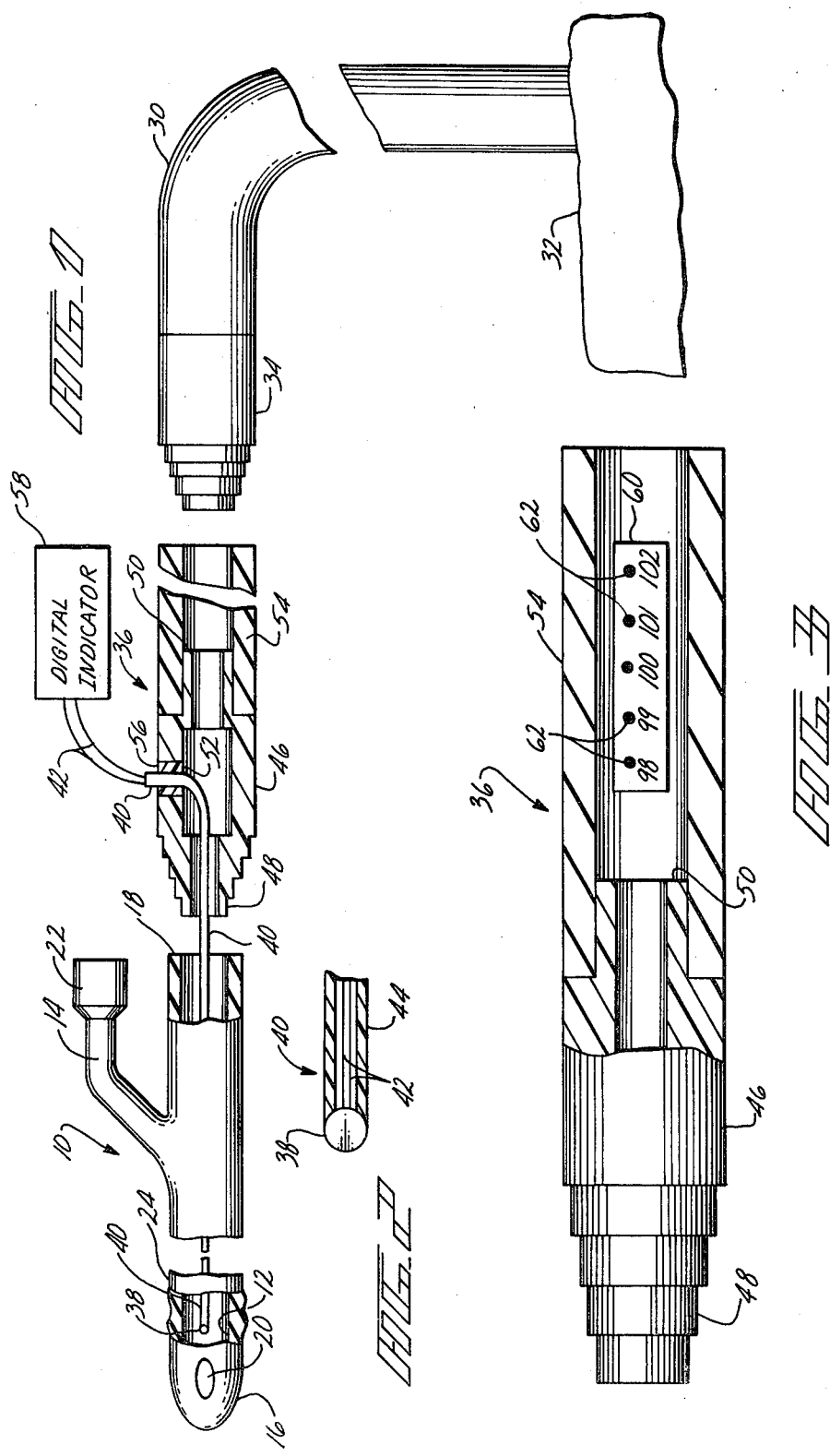

METHOD AND APPARATUS FOR MONITORING BODY CONDITIONS

BACKGROUND OF THE INVENTION

This invention relates to the measurement of body conditions and, more particularly, to a method and apparatus for monitoring body conditions, such as core temperature.

Core body temperature is an important indicator of a patient's body functions and conditions, such as for example, shock. A thermometer placed in the ear, nose, mouth, or rectum measures peripheral temperature, which is affected by extraneous factors such as ambient temperature and body circulation. Therefore, peripheral temperature is not an accurate indicator of core temperature. In order to provide an accurate indication of core temperature, it has been proposed to embed a temperature sensor in the wall of a urinary catheter at the extremity thereof inserted into the bladder. Electrical leads extend longitudinally through the wall of the catheter to an indicator outside the patient's body. The described catheter with embedded temperature sensor is substantially more expensive than a conventional catheter. For this reason it is desirable to use the described catheter selectively only on patients who require core temperature monitoring. However, it is commonly not known at the time the catheter is inserted in a patient whether or not core temperature monitoring should be prescribed.

SUMMARY OF THE INVENTION

The invention permits core temperature or other body function to be measured after a conventional urinary catheter has been inserted in a patient.

One aspect of the invention is a method comprising the steps of feeding a flexible transmission line having a sensor connected to its end into the outlet opening of a catheter until the sensor lies near the inlet thereof, connecting the other end of the transmission line to an indicator outside the catheter, and connecting a drainage tube to the outlet of the catheter without fluid leakage at the point of egress of the transmission line. Thus, when the decision is made to monitor a body condition, such as core temperature, a sensor can be set into place after the catheter has been inserted into the patient. The sensor can be removed at any time and reused if desired.

Another aspect of the invention is body monitoring apparatus for use with a catheter tube having an outlet opening and a drainage tube having a male connector engageable with the outlet opening of the catheter tube. The apparatus comprises a tubular body member having at one end a male connector engageable with the outlet opening of the catheter tube, at the other end an outlet opening engageable with the male connector of the drainage tube, and an exit from the body member between the connector and the outlet opening. A flexible transmission line extends from a condition sensing transducer such as a temperature sensor through the body member from the male connector thereof through the exit to a point outside the body member. The exit is sealed to prevent leakage of fluid at the point of egress of the transmission line.

Another aspect of the invention is a temperature monitoring system in which an intermediate tube is removably connectable between the outlet of a catheter and the inlet of a drainage tube. The intermediate tube has a window to permit outside observation of the interior of the tube. One or more temperature responsive visual indicators are located in the intermediate tube at the window. The indicators respond to different temperatures. Since urine temperature flowing through the intermediate tube is being measured by this technique, it is not as accurate as measurement with a temperature sensor near the inlet end of the catheter.

BRIEF DESCRIPTION OF THE DRAWINGS

The features of specific embodiments of the best mode contemplated of carrying out the invention are illustrated in the drawings, in which:

FIG. 1 is a side partially sectional view of a temperature monitoring system incorporating the principles of the invention;

FIG. 2 is an enlarged partially sectional view of the temperature sensor and part of the transmission line of FIG. 1; and FIG. 3 is a side partially sectional view of an alternative embodiment of an intermediate tube for use in practice of the invention.

DETAILED DESCRIPTION OF THE SPECIFIC EMBODIMENTS

In FIGS. 1 and 2, a conventional urinary retention catheter tube 10 is shown. A commercially available Curity Foley catheter manufactured by the Kendall Company, Code No. 2710, is typical of this type of catheter tube. Catheter tube 10 comprises in a one-piece, molded and bonded rubber construction a urine passage 12 and a balloon filling conduit 14. Catheter tube 10 has an interior end 16 adapted to be inserted into the urethra of a patient until it lies in the bladder and an external end 18 lying outside the patient. Eye openings 20 at internal end 16 serve as an inlet to urine passage 12. The outlet of urine passage 12 is at external end 18. Passage 12 extends continuously between ends 16 and 18. Conduit 14 also extends continuously between a one-way valve 22 at end 18 and a thin walled sleeve 24 at end 16, which serves as a retention balloon when inflated. After catheter 10 is inserted into the patient's urethra until end 16, including sleeve 24, lies in the patient's bladder, a fluid, preferably sterilized water, is injected by a syringe into tube 14 via valve 22, thereby inflating sleeve 24 and retaining catheter 10 in place. End 18 is coupled to a drainage tube 30, which leads to a urine drainage bag 32.

End 18 has an outlet opening into which a male connector 34 on the end of tube 30 removably fits to engage the outlet opening with connector 34. The invention involves monitoring the core temperature of a patient with catheter tube 10 in place by means of body monitoring apparatus insertable in the fluid line between catheter tube 10 and drainage tube 30. In the embodiment of FIGS. 1 and 2, the apparatus comprises an intermediate tube 36, a temperature sensor 38, and a transmission line 40.

Sensor 38 could comprise a thermistor operating in the self-heated mode. As depicted in FIG. 2, transmission line 40 could comprise a pair of electrically conductive mutually insulated leads 42 inside a sheath 44. Leads 42 could be insulated from each other by dipping them individually into an electrically insulative varnish. Sensor 38 is bonded to the end of sheath 44 which could be made of a plastic tubing.

Body member 36 could comprise a flexible transparent plastic tube 54 and a rigid molded plastic piece 46 having a male connector 48 at one end, a stepped reduced diameter portion 50 at the other end, and an exit opening 52 therebetween. Tube 54 is secured to portion 50, such as for example by bonding. Connector 48 is identical to connector 34 so it can removably engage the outlet opening of catheter 10 and the inside diameter of tube 54 is the same as the outlet opening of catheter 10 so it can removably engage connector 34. Transmission line 40 extends from sensor 38 through piece 46 from connector 48 to exit 52, which serves as the point of egress of transmission line 40 from body member 36. A plug of water impervious epoxy 56 fills the space in exit 52 around transmission line 40, thereby sealing exit 52 and securing transmission line 40 to piece 46. Sheath 44 ends at a convenient point outside body member 36 and leads 42 are connected to a digital indicator 58 of conventional construction.

To measure core body temperature after catheter 10 has been inserted into the urethra of a patient, connector 34 of drainage tube 30 is first disconnected from the outlet opening of catheter tube 10. Second, sensor 38 is introduced into the outlet opening of catheter tube 10 and advanced through catheter 10 to its inlet by feeding transmission line 40 into catheter tube 10. Third, connector 48 is made to engage the outlet opening of catheter tube 10. Finally, connector 34 is made to engage the outlet opening of body member 36. The portion of transmission line 40 extending from connector 48 is sufficiently long for sensor 38 to lie near the inlet of catheter tube 10, preferably between eyes 20 and sleeve 24 when body member 36 is installed between catheter tube 10 and drainage tube 30, to insure that sensor 38 lies within the bladder of the patient. Sensor 38 produces an electrical output that is transmitted by leads 42 to digital indicator 58. Sensor 38 can be removed for reuse simply by disconnecting body member 36 from the line between catheter tube 10 and drainage tube 30 and reconnecting the latter directly together once again.

In the embodiment of FIG. 3, body member 36 has no exit opening because no transmission line is required. In this case the urine temperature is measured within body member 36. A temperature indicator 60, in the form of a plastic substrate for example, has a plurality of dot shaped indicating elements 62 thereon. Indicator 60 is bonded to the inner side wall of tube 54. Each of elements 62 provides a visual indication responsive to a different temperature, as indicated by a number directly below such element. Thus, the element above "number 98" provides a visual indication when the urine temperature is 98°, etc. Indicator 60 is mounted in body member 36 at a window in the form of the transparent walls of tube 54. Indicator elements 62 could comprise commercially available temperature recorders sold by Telatemp Corporation, of Fullerton, Calif., or liquid cholesteric crystals. It is preferable to so orient body member 36 as to collect urine therein for measurement purposes rather than to measure continuously flowing urine.

The described embodiment of the invention is only considered to be preferred and illustrative of the inventive concept; the scope of the invention is not to be restricted to such embodiment. Various and numerous other arrangements may be devised by one skilled in the art without departing from the spirit and scope of this invention.

What is claimed is:

1. Body monitoring apparatus for use with a urinary catheter tube having an outlet opening and a drainage tube having a male connector engageable with the outlet opening of the catheter tube, the apparatus comprising:
   a tubular body member having at one end a male connector engageable with the outlet opening of the catheter tube, at the other end an outlet opening engageable with the male connector of the drainage tube, and an exit from the body member between the connector and the outlet opening;
   a temperature sensing transducer producing an electrical output, the transducer being located outside the body member;
   a flexible transmission line extending from the transducer through the body member from the male connector thereof through the exit to a point outside the body member to transmit the electrical output outside the body member; and
   means for sealing the exit.

2. The apparatus of claim 1, in which the transducer is a thermistor.

3. The apparatus of claim 2, in which the transmission line comprises a pair of lead wires each connected at one end to the thermistor and a protective sheath around the lead wires.

4. A temperature monitoring system comprising:
   a urinary catheter tube having an inlet and an outlet;
   a drainage tube having an inlet;
   an intermediate tube removably connectable between the outlet of the catheter tube and the inlet of the drainage tube;
   an electrical temperature sensor in the passage of the catheter tube adjacent the catheter inlet for producing an electrical output;
   an indicator; and
   a pair of flexible leads connected at one end to the temperature sensor and at the other end to the indicator to convey the electrical output to the indicator, the leads extending from the sensor through the catheter passage into the intermediate tube and through the wall of the intermediate tube to the indicator such that the leads can be run through the catheter tube until the sensor lies near the inlet while the indicator is outside the catheter tube.

5. The system of claim 4, in which the inlet of the drainage tube has a male connector engageable with the outlet of the catheter tube and the intermediate tube has at one end a male connector engageable with the outlet of the catheter tube and at the other end an outlet opening engageable with the male connector of the drainage tube.

6. A temperature monitoring system comprising:
   a urinary catheter tube having an inlet and an outlet;
   a drainage tube having an inlet;
   a temperature sensor producing an electrical output, the temperature sensor being located in proximity to the inlet of the catheter;
   an intermediate tube removably connected between the outlet of the catheter tube and the inlet of the drainage tube, the intermediate tube having an exit for leads between its ends;
   an indicator disposed outside the tubes;
   a pair of flexible leads connected at one end to the temperature sensor and at the other end to the indicator to convey the electrical signal to the indicator, the leads extending from the sensor within the catheter tube and the intermediate tube and through the exit from inside to outside the intermediate tube; and means for sealing the exit.

7. A method for monitoring a body condition using a urinary catheter tube with an inlet and an outlet opening, a drainage tube, and an intermediate tube with open ends and an exit between its open ends, the intermediate tube including a condition sensing transducer being located outside the intermediate tube and producing an electrical output, a flexible transmission line extending from the transducer through the body member from one end thereof through the exit to a point outside the body member to transmit the electrical output outside the body member, and means for sealing the exit, the method comprising in the order recited in steps of:

inserting the catheter tube into the urethra of a patient;

feeding the transmission line into the outlet opening of the catheter tube until the transducer lies near the inlet of the catheter tube;

connecting the one end of the intermediate tube to the outlet opening of the catheter tube; and connecting the other end of the intermediate tube to the drainage tube.

8. The method of claim 7, in which the feeding step feeds a temperature sensing transducer into the catheter.

* * * * *